US009452229B2

(12) United States Patent
Nalepa et al.

(10) Patent No.: US 9,452,229 B2
(45) Date of Patent: Sep. 27, 2016

(54) HIGHLY CONCENTRATED, BIOCIDALLY ACTIVE COMPOSITIONS AND AQUEOUS MIXTURES AND METHODS OF MAKING THE SAME

(75) Inventors: Christopher J. Nalepa, Baton Rouge, LA (US); Farah D. Azarnia, Baton Rouge, LA (US)

(73) Assignee: ALBEMARLE CORPORATION, Baton Rouge, LA (US)

( * ) Notice: Subject to any disclaimer, the term of this patent is extended or adjusted under 35 U.S.C. 154(b) by 2128 days.

(21) Appl. No.: 11/439,571

(22) Filed: May 23, 2006

(65) Prior Publication Data

US 2006/0278586 A1    Dec. 14, 2006

Related U.S. Application Data

(60) Provisional application No. 60/753,284, filed on Dec. 21, 2005, provisional application No. 60/689,737, filed on Jun. 10, 2005.

(51) Int. Cl.
| | | |
|---|---|---|
| *A01N 59/00* | (2006.01) | |
| *A01N 25/00* | (2006.01) | |
| *A01N 25/02* | (2006.01) | |
| *A01N 25/22* | (2006.01) | |
| *A01N 41/06* | (2006.01) | |
| *A61L 2/18* | (2006.01) | |
| *C02F 1/76* | (2006.01) | |

(52) U.S. Cl.
CPC ............... *A61L 2/18* (2013.01); *A01N 59/00* (2013.01); *C02F 1/766* (2013.01)

(58) Field of Classification Search
CPC ...... A01N 59/00; A01N 25/02; A01N 25/22; A01N 25/00; A01N 2300/00; A61L 2/18; C02F 1/766
USPC ................................. 424/405, 723; 210/754
See application file for complete search history.

(56) References Cited

U.S. PATENT DOCUMENTS

| | | |
|---|---|---|
| 3,152,073 A | 10/1964 | Morton |
| 3,170,883 A | 2/1965 | Owen et al. |
| 3,222,276 A | 12/1965 | Belohlav et al. |
| 3,308,062 A | 3/1967 | Gunther |
| 3,328,294 A | 6/1967 | Self et al. |
| 3,412,021 A | 11/1968 | Paterson |
| 3,558,503 A | 1/1971 | Goodenough et al. |
| 3,589,859 A | 6/1971 | Foroulis |
| 3,711,246 A | 1/1973 | Foroulis |
| 3,749,672 A | 7/1973 | Golton et al. |
| 3,767,586 A | 10/1973 | Rutkiewic |
| 4,032,460 A | 6/1977 | Zilch et al. |
| 4,237,090 A | 12/1980 | DeMonbrun et al. |
| 4,295,932 A | 10/1981 | Pocius |
| 4,382,799 A | 5/1983 | Davis et al. |
| 4,427,435 A | 1/1984 | Lorenz |
| 4,451,376 A | 5/1984 | Sharp |
| 4,465,598 A | 8/1984 | Darlington et al. |
| 4,476,930 A | 10/1984 | Watanabe |
| 4,490,308 A | 12/1984 | Fong et al. |
| 4,491,507 A | 1/1985 | Herklotz et al. |
| 4,539,071 A | 9/1985 | Clifford et al. |
| 4,546,156 A | 10/1985 | Fong et al. |
| 4,566,973 A | 1/1986 | Masler, III et al. |
| 4,595,517 A | 6/1986 | Abadi |
| 4,595,691 A | 6/1986 | LaMarre et al. |
| 4,604,431 A | 8/1986 | Fong et al. |
| 4,642,194 A | 2/1987 | Johnson |
| 4,643,835 A | 2/1987 | Koeplin-Gall et al. |
| 4,661,503 A | 4/1987 | Martin et al. |
| 4,680,339 A | 7/1987 | Fong |
| 4,703,092 A | 10/1987 | Fong |
| 4,711,724 A | 12/1987 | Johnson |
| 4,752,443 A | 6/1988 | Hoots et al. |
| 4,759,852 A | 7/1988 | Trulear |
| 4,762,894 A | 8/1988 | Fong et al. |
| 4,777,219 A | 10/1988 | Fong et al. |
| 4,801,388 A | 1/1989 | Fong et al. |
| 4,802,990 A | 2/1989 | Inskeep, Jr. |
| 4,822,513 A | 4/1989 | Corby |
| 4,846,979 A | 7/1989 | Hamilton |
| 4,883,600 A | 11/1989 | MacDonald et al. |
| 4,886,915 A | 12/1989 | Favstrtsky |
| 4,898,686 A | 2/1990 | Johnson et al. |
| 4,898,975 A | 2/1990 | Favstritsky |
| 4,906,651 A | 3/1990 | Hsu |
| 4,923,634 A | 5/1990 | Hoots et al. |
| 4,929,424 A | 5/1990 | Meier et al. |

(Continued)

FOREIGN PATENT DOCUMENTS

| | | |
|---|---|---|
| EP | 0 819 647 A2 | 1/1998 |
| EP | 1 080 641 A2 | 3/2001 |

(Continued)

OTHER PUBLICATIONS

Donald L. Hall, S. Michael Sterner and Robert J. Bodnar, "Freezing point depression of NaCl—KCl—H2O solutions", Economic Geology, 1988, 83(1), 197-202.*

Hicks, W. B., "Solubility of Mixtures of Sodium and Potassium Chlorides in Solutions of Hydrochloric Acid", Journal of the American Chemical Society, 1915, vol. 37, No. 4, p. 844-847 (4 pages).

Bruce S. Ault, et al.; "Infrared and Raman Spectra of the M+Cl3— Ion Pairs and Their Chlorine—Bromine Counterparts Isolated in Argon Matrices"; Journal of Chemical Physics, 1976, vol. 64, No. 12, pp. 4853-4859; American Institute of Physics, Melfville, New York, USA.

Hobart H. Willard, et al.; "Elementary Quantitative Analysis", Third Edition, Chapter XIV, 1933, pp. 261-271; D. Van Nostrand Company, Inc., New York, New York, USA.

*Primary Examiner* — John Pak
*Assistant Examiner* — Nathan W Schlientz
(74) *Attorney, Agent, or Firm* — Marcy M. Hoefling

(57) ABSTRACT

The present invention relates to liquid mixtures and compositions having high bromine concentrations that find use as biocides and processes for preparing them.

28 Claims, No Drawings

(56) References Cited

U.S. PATENT DOCUMENTS

| | | |
|---|---|---|
| 4,929,425 A | 5/1990 | Hoots et al. |
| 4,966,716 A | 10/1990 | Favstritsky et al. |
| 4,992,209 A | 2/1991 | Smyk |
| 4,995,987 A | 2/1991 | Whitekettle et al. |
| 5,034,155 A | 7/1991 | Soeder et al. |
| 5,035,806 A | 7/1991 | Fong |
| 5,047,164 A | 9/1991 | Corby |
| 5,055,285 A | 10/1991 | Duncan et al. |
| 5,118,426 A | 6/1992 | Duncan et al. |
| 5,120,452 A | 6/1992 | Ness et al. |
| 5,120,797 A | 6/1992 | Fong et al. |
| 5,141,652 A | 8/1992 | Moore et al. |
| 5,179,173 A | 1/1993 | Fong et al. |
| 5,192,459 A | 3/1993 | Tell et al. |
| 5,194,238 A | 3/1993 | Duncan et al. |
| 5,196,126 A | 3/1993 | O'Dowd |
| 5,202,047 A | 4/1993 | Corby |
| 5,259,985 A | 11/1993 | Nakanishi et al. |
| 5,264,136 A | 11/1993 | Howarth et al. |
| 5,389,384 A | 2/1995 | Jooste |
| 5,424,032 A | 6/1995 | Christensen et al. |
| 5,443,849 A | 8/1995 | Corby |
| 5,464,636 A | 11/1995 | Hight et al. |
| 5,525,241 A | 6/1996 | Clavin et al. |
| 5,527,547 A | 6/1996 | Hight et al. |
| 5,589,106 A | 12/1996 | Shim et al. |
| 5,607,619 A | 3/1997 | Dadgar et al. |
| 5,679,239 A | 10/1997 | Blum et al. |
| 5,683,654 A | 11/1997 | Dallmier et al. |
| 5,795,487 A | 8/1998 | Dallmier et al. |
| 5,900,512 A | 5/1999 | Elnagar et al. |
| 5,922,745 A | 7/1999 | McCarthy et al. |
| 5,942,126 A | 8/1999 | Dallmier et al. |
| 6,007,726 A | 12/1999 | Yang et al. |
| 6,015,782 A | 1/2000 | Petri et al. |
| 6,037,318 A | 3/2000 | Na et al. |
| 6,068,861 A | 5/2000 | Moore et al. |
| 6,110,387 A | 8/2000 | Choudhury et al. |
| 6,123,870 A | 9/2000 | Yang et al. |
| 6,136,205 A | 10/2000 | Dallmier |
| 6,156,229 A | 12/2000 | Yang et al. |
| 6,270,722 B1 | 8/2001 | Yang et al. |
| 6,287,473 B1 | 9/2001 | Yang et al. |
| 6,299,909 B1 | 10/2001 | Moore et al. |
| 6,306,441 B1 | 10/2001 | Moore et al. |
| 6,322,749 B1 | 11/2001 | McCarthy et al. |
| 6,322,822 B1 | 11/2001 | Moore et al. |
| 6,348,219 B1 | 2/2002 | Torres et al. |
| 6,352,725 B1 | 3/2002 | Torres et al. |
| 6,375,991 B1 | 4/2002 | Moore, Jr. |
| 6,419,879 B1 | 7/2002 | Cooper et al. |
| 6,423,267 B1 | 7/2002 | Yang et al. |
| 6,478,972 B1 | 11/2002 | Shim et al. |
| 6,495,169 B1 | 12/2002 | Moore, Jr. et al. |
| 6,506,418 B1 | 1/2003 | McKinnie et al. |
| 6,511,682 B1 | 1/2003 | Moore, Jr. et al. |
| 6,533,958 B2 | 3/2003 | Shim et al. |
| 6,551,624 B2 | 4/2003 | Moore, Jr. |
| 6,620,441 B1 | 9/2003 | Kendall et al. |
| 6,652,889 B2 | 11/2003 | Moore, Jr. |
| 6,869,620 B2 | 3/2005 | Moore, Jr. |
| 7,087,251 B2 | 8/2006 | Nalepa |
| 2002/0110603 A1 | 8/2002 | Moore, Jr. et al. |
| 2004/0144702 A1 | 7/2004 | Zimmerman et al. |

FOREIGN PATENT DOCUMENTS

| | | |
|---|---|---|
| WO | WO 90/15780 A1 | 12/1990 |
| WO | WO 96/14092 A1 | 5/1996 |
| WO | WO 96/30562 A1 | 10/1996 |
| WO | WO 97/20546 A1 | 6/1997 |
| WO | WO 97/20909 A1 | 6/1997 |
| WO | WO 97/34827 A1 | 9/1997 |
| WO | WO 97/43392 A1 | 11/1997 |
| WO | WO 98/15609 A1 | 4/1998 |
| WO | WO 99/06320 A1 | 2/1999 |
| WO | WO 99/32596 A1 | 7/1999 |
| WO | WO 99/55627 A1 | 11/1999 |
| WO | WO 99/62339 A1 | 12/1999 |
| WO | WO 00/34186 A1 | 6/2000 |
| WO | WO 00/58532 A1 | 10/2000 |
| WO | WO 01/20996 A1 | 3/2001 |
| WO | WO 01/35746 A1 | 5/2001 |
| WO | WO 03/093171 A1 | 11/2003 |

\* cited by examiner

HIGHLY CONCENTRATED, BIOCIDALLY ACTIVE COMPOSITIONS AND AQUEOUS MIXTURES AND METHODS OF MAKING THE SAME

REFERENCE TO RELATED APPLICATIONS

This application claims priority to U.S. Provisional Patent Application No. 60/753,284 filed Dec. 21, 2005, and U.S. Provisional Patent Application No. 60/689,737 filed Jun. 10, 2005, the disclosure of both herein incorporated by reference in their entirety.

FIELD OF THE INVENTION

The present invention relates to mixtures and compositions that find use as biocides. More particularly, the present invention relates to liquid mixtures and compositions having high bromine concentrations that find use as biocides and processes for preparing them.

BACKGROUND OF THE INVENTION

Bromine-based biocides have proven biocidal advantages over chlorination-dechlorination for the microbiological control of cooling waters and disinfection of waste treatment systems. The water treatment industry recognizes these advantages to be cost-effective microbiological control at higher pH values, almost no loss in biocidal activity in the presence of ammonia, and effective control of bacteria, algae and mollusks.

One such bromine-based biocide is disclosed in U.S. Pat. No. 6,652,889, which is incorporated herein in its entirety. In the '889 patent, it is taught to add sodium hydroxide and sulfamic acid to water to form an aqueous solution of alkali metal salt of sulfamic acid. To the aqueous solution of alkali metal salt of sulfamic acid is added bromine chloride or bromine to form a concentrated biocide formulation.

However, bromine-based biocides such as those disclosed in the '889 patent do not have a bromine concentration high enough for some applications. Further, highly concentrated bromine-based biocides have been previously thought difficult to make. It was thought that at higher concentrations of bromine, the biocide would no longer be a liquid.

Thus, there is a need in the art for a bromine based composition or mixture that finds use as a biocidal agent and has a concentration of bromine higher than those currently available in the art, but still remains a liquid despite the high concentration of active bromine.

SUMMARY OF THE INVENTION

The present invention relates to a composition that is a derivative of at least:
i) a nitrogen containing stabilizer;
ii) at least two metal cation bases, the metal cations of said at least two metal bases selected from Group IA, Group IIA, and mixtures thereof; and,
iii) a $Br^+$ source, a $Cl^+$ source, or mixtures thereof;
   wherein said composition has an active bromine content of between about 100,000 ppm (wt./wt.) and 220,000 ppm (wt./wt.), and the pH of the composition is at least 7.

In another embodiment, the present invention relates to a mixture comprising predominantly at least two metal salts of a) bromo sulfamate; b) chloro sulfamate; c) halides; d) sulfamates; and e) hydroxides wherein said metal salts have a metal component selected from Group IA, Group IIA, and mixtures thereof, and said mixture has an active bromine content of between about 100,000 ppm (wt./wt.) and 220,000 ppm (wt./wt.) and a pH of at least 7.

In one embodiment, the present invention relates to a process comprising:
a) mixing, in the presence of water, i) sulfamic acid, ii) at least two metal bases; and iii) a $Br^+$ source, a $Cl^+$, or mixtures thereof thereby forming an aqueous mixture comprising at least soluble and insoluble metal halide salts; and
b) removing at least a portion of the insoluble metal halide salts from said aqueous mixture,
   wherein i), ii), and iii) are mixed in proportions such that the aqueous mixture comprises predominantly at least two metal salts of a) bromo sulfamate; b) chloro sulfamate; c) halides; d) sulfamates; and e) hydroxides wherein said metal component of said at least two metal salts and said at least two metal bases are selected from Group IA, Group IIA, and mixtures thereof, and said aqueous mixture has an active bromine content of between about 100,000 ppm (wt./wt.) and 220,000 ppm (wt./wt.) and a pH of at least 7.

In another embodiment, the present invention relates to a process comprising:
a) mixing, in the presence of water, i) at least one metal salt of sulfamic acid, ii) at least one metal base; and iii) a $Br^+$ source, a $Cl^+$, or mixtures thereof thereby forming an aqueous mixture comprising metal halide salts; and
b) removing at least a portion of said metal halide salts from said aqueous mixture,
   wherein the metal cation of the at least one metal base ii) is different from that of the at least one metal salt of sulfamic acid i), and i), ii), and iii) are mixed in proportions such that the aqueous mixture comprises predominantly at least two metal salts of a) bromo sulfamate; b) chloro sulfamate; c) halides; d) sulfamates; and e) hydroxides; wherein the metal component of said at least two metal salts and said at least two metal bases are selected from Group IA, Group IIA, and mixtures thereof, and said aqueous mixture has an active bromine content of between about 100,000 ppm (wt./wt.) and 220,000 ppm (wt./wt.) and a pH of at least 7.

DETAILED DESCRIPTION OF THE INVENTION

The term "active bromine" as used herein refers to all $Br^+$-containing species that are capable of biocidal activity. It is generally accepted in the art that all of the bromine in the +1 oxidation state is biocidally active and is thus included in the term "active bromine". As is well known in the art, bromine, bromine chloride, hypobromous acid, hypobromite ion, hydrogen tribromide, tribromide ion, and N-brominated compounds have bromine in the +1 oxidation state. Thus, these, as well as other such species to the extent they are present, constitute the active bromine content of the compositions of this invention, i.e. $Br^+$ herein. See, for example, U.S. Pat. Nos. 4,382,799 and 5,679,239. A well-established method in the art for determining the amount of active bromine in a solution is starch-iodine titration, which determines all of the active bromine in a sample, regardless of what species may constitute the active bromine. The usefulness and accuracy of the classical starch-iodine method for quantitative determination of bromine and many other oxidizing agents has long been known, as witness Chapter XIV of Willard-Furman, Elementary Quantitative Analysis, Third Edition, D. Van Nostrand Company, Inc., New York, Copyright 1933, 1935, 1940.

A typical starch-iodine titration to determine active bromine is carried out as follows: A magnetic stirrer and 50 milliliters of glacial acetic acid are placed in an iodine flask. The sample (usually about 0.2-0.5 g) for which the active bromine is to be determined is weighed and added to the flask containing the acetic acid. Water (50 milliliters) and aqueous potassium iodide (15% (wt./wt.); 25 milliliters) are then added to the flask. The flask is stoppered using a water seal. The solution is then stirred for fifteen minutes, after which the flask is unstoppered and the stopper and seal area are rinsed into the flask with water. An automatic buret (Metrohm Limited) is filled with 0.1-normal sodium thiosulfate. The solution in the iodine flask is titrated with the 0.1-normal sodium thiosulfate; when a faint yellow color is observed, one milliliter of a 1% (wt./wt.) starch solution in water is added, changing the color of the solution in the flask from faint yellow to blue. Titration with sodium thiosulfate continues until the blue color disappears. The amount of active bromine is calculated using the weight of the sample and the volume of sodium thiosulfate solution titrated. Thus, the amount of active bromine in a composition of this invention, regardless of actual chemical form, can be quantitatively determined. "Active bromine content" as used herein is based on BrCl as the reference.

It should also be noted that "nitrogen-containing stabilizer" as used herein refers to amide derivatives of carbonic acid, hydrogen cyanide, carboxylic acid, amino acid, sulfuric acid, phosphoric acid, and boric acid. Non-limiting examples of nitrogen-containing stabilizers suitable for use herein include urea, thiourea, creatinine, cyanuric acids, alkyl hydantoins, mono- or di-ethanolamine, organic sulfonamides, biuret, sulfamic acid and salts thereof, organic sulfamic acid and melamine. Preferably, the nitrogen-containing stabilizer used herein is sulfamic acid.

In one embodiment, the present invention relates to a composition, which can be made by any process described herein, that is a derivative of at least i) a nitrogen containing stabilizer; and ii) at least two metal cation bases; and iii) a $Br^+$ source, a $Cl^+$ source, or mixtures thereof. $Br^+$ sources as used herein is meant to refer to those described above. $Cl^+$ sources include elemental chlorine ($Cl_2$), hypochlorite compounds such as sodium hypochlorite solution (bleach), lithium hypochlorite, or calcium hypochlorite, and N-chlorinated compounds such as trichloroisocyanuric acid and sodium dichloroisocyanurate.

The at least two, preferably only two, metal cation salts of the present invention have a metal cation that is suitably selected from Group IA, Group IIA, and mixtures thereof, of the Periodic Table of the Elements. The composition has an active bromine content of between about 100,000 ppm (wt./wt.) and 220,000 ppm (wt./wt.) and a pH of at least 7. In some embodiments, the pH of the composition is in the range of from about 10 to about 14, and preferably in the range of from about 12 to about 14. In some embodiments, the pH is in the range of from about 12.5 to about 14. It is preferred that the active bromine content of the composition is in the range of from about 125,000 ppm (wt./wt.) to about 220,000 ppm (wt./wt.), more preferably in the range of from greater than 145,000 ppm (wt./wt.) to about 220,000 ppm (wt./wt.). In another embodiment, the active bromine content is in the range of from greater than 160,000 ppm (wt./wt.) to about 220,000 ppm (wt./wt.).

In another embodiment, the present invention relates to a mixture comprising predominantly at least two metal salts of a) bromo sulfamate; b) chloro sulfamate; c) halides; d) sulfamates; and e) hydroxides wherein said metal salts have a metal component selected from Group IA, Group IIA, and mixtures thereof, of the Periodic Table of the Elements. This mixture has an active bromine content of between about 100,000 ppm (wt./wt.) and 220,000 ppm (wt./wt.) wherein the pH of the liquid biocide is at least 7. It is preferred that the active bromine content of the composition is in the range of from about 125,000 ppm (wt./wt.) to about 220,000 ppm (wt./wt.), more preferably in the range of from greater than 145,000 ppm (wt./wt.) to about 220,000 ppm (wt./wt.). In another embodiment, the active bromine content is in the range of from greater than 160,000 ppm (wt./wt.) to about 220,000 ppm (wt./wt.)

The mixture and/or composition of the present invention can suitably be made by mixing, in the presence of water, i) sulfamic acid, ii) at least two metal bases, and iii) a $Br^+$ source, a $Cl^+$ source, or mixtures thereof, preferably BrCl, thereby forming an aqueous mixture comprising at least soluble and insoluble metal halide salts. In a preferred embodiment, component i) is first mixed with water, and the at least two metal bases ii) are then mixed into the sulfamic acid-containing water, and component iii) is then introduced.

At least a portion, preferably substantially all, of the insoluble metal halide salts is removed from the aqueous mixture. By "insoluble metal halide salts" it is meant metal halide salts that are insoluble in the aqueous mixture. Insoluble metal halide salts present in the aqueous mixture typically include the metal cation selected from Group IA, IIA, and mixtures thereof, in combination with Br and/or Cl. The method by which the insoluble metal halide salts are removed is not critical to the instant invention and can be suitably selected from any means known to be effective at removing solid particles from a liquid. Non-limiting examples of suitable methods include mechanical filtration utilizing materials such as filter cloths, screens, plugs, etc. In preferred embodiments, the at least a portion of insoluble metal halide salts are removed from the aqueous mixture by filtration.

In the process suitable for producing the mixture and/or composition of the present invention, components i), ii), and iii) are mixed in proportions resulting in the formation of an aqueous mixture comprising predominantly at least two metal salts of a) bromo sulfamate; b) chloro sulfamate; c) halides; d) sulfamates; and e) hydroxides. The filtered aqueous mixture has an active bromine content and pH as described above, including preferred ranges.

In another embodiment, the mixture and/or composition can be formed by a process that comprises mixing, in the presence of water, i) at least one, preferably one, metal salt of sulfamic acid, ii) at least one metal base, and iii) a $Br^+$ source, a $Cl^+$ source, or mixtures thereof, preferably BrCl thereby forming an aqueous mixture comprising metal halide salts. At least a portion of the metal halide salts contained therein is removed from the aqueous mixture. Filtration methods used in this embodiment can be selected from any of those described above, including preferred embodiments.

One desirable way of accomplishing the mixing of components i), ii), and iii) comprises concurrently introducing them into a reaction zone, such as a reactor or other reaction vessel, to form an aqueous mixture having a pH of at least 7, in some embodiments in the range of about 10 to about 14, and preferably in the range of about 12 to about 14, more preferably in the range of 12.5 to about 14. As noted above, the proportions of i), ii), and iii) used are such that the active bromine content of the resulting aqueous mixture is in the range described above, including preferred embodiments. Also, in some embodiments, the relative proportions of i), ii), and iii) are such that the atomic ratio of nitrogen to active bromine of the mixture and/or composition is greater than 1, preferably in the range of about 1.05 to about 1.4, and more preferably in the range of from about 1.1 to about 1.3. Still higher ratios can be employed, if desired.

In this embodiment, it is preferred that the metal cation of the metal base, component ii), is different from that of the metal salt of sulfamic acid, component i). In this embodiment, components i), ii), and iii) are mixed in proportions such that the aqueous mixture comprises predominantly at least two metal salts of a) bromo sulfamate; b) chloro sulfamate; c) halides; d) sulfamates; and e) hydroxides. The aqueous mixture thus formed has an active bromine content and pH as described above, including preferred embodiments.

In some embodiments, it may be desirable to maintain the desired pH of the resulting composition and/or aqueous mixture at or above 7 by also introducing (continuously or intermittently, as desired) additional metal base. Non-limiting examples of ways to introduce the additional metal base used to control the pH are by a co-feed of an aqueous solution of metal base, or by separately adding the base into the solution. When the composition and/or aqueous mixture is to be stored in drums, it is desirable to have the pH of such at about 10 or above, and preferably in the range of about 12.5 to about 14.

Metals suitable for use as cations in metal bases, cations in metal salts of sulfamic acid, metal salts of a) bromo sulfamate; b) chloro sulfamate; c) halides; d) sulfamates, and e) hydroxides and/or components used to make any the above, can be suitably selected from Group IA and Group IIA, preferably Group IA, of the Periodic Table of the Elements. If the metal cation is a component of a metal base, it is coupled with an oxide or hydroxide group, preferably a hydroxide group. In preferred embodiments, the at least two metal bases are sodium hydroxide and at least one of lithium hydroxide and potassium hydroxide. In particularly preferred embodiments, the metal bases used are sodium hydroxide in combination with potassium hydroxide or sodium hydroxide in combination with lithium hydroxide. Thus, the metal cations used in any of the above can be any of those selected from Group IA and Group IIA, preferably Group IA, of the Periodic Table of the Elements.

The inventors hereof have unexpectedly discovered that by using at least two metal bases, or metal salts of a nitrogen-containing stabilizer, during the formation of the compositions, mixtures and/or liquid biocides of the present invention, compositions, mixtures and/or liquid biocides of high active bromine content can be made that remain liquid at room temperature.

In preferred embodiments, the inventors hereof have also unexpectedly discovered that by using at least two metal bases, or metal salts of a nitrogen-containing stabilizer, during the formation of the compositions, mixtures and/or liquid biocides of the present invention, compositions, mixtures and/or liquid biocides having low temperature properties superior to those currently available is achieved. These low temperature properties include freezing point temperatures lower than about 10° C., preferably lower than about 5° C., more preferably lower than about 0° C., and most preferably lower than about −5° C. In one embodiment, the freezing point temperature ranges from about −5° C. to about −5° C. It should be noted that the freezing point temperatures described herein are those determined by the method discussed below.

The freezing point temperature of a liquid biocide, compositions and/or mixture according to the present invention can be determined according to the following method. It should be noted that "freezing point" and "freeze point" can be used interchangeably herein, and they are both used in the broadest sense. Thus, they include "crystallization temperature" within their definitions also. In this method, an approximately 30 ml sample of liquid biocide, composition and/or mixture is placed in a jacketed glass tube, and a rubber stopper/thermometer/helical stirrer assembly is inserted into the glass tube such that the tip of the thermometer is positioned about a half an inch from the bottom of the tube. The glass tube is then placed into a circulating, ethylene glycol cooling bath equipped with a temperature probe. It should be noted that care should be taken to ensure that the temperature probe does not contact the bottom or sides of the cooling bath, and the glass tube should be supported such that the level of the sample and ethylene glycol are approximately equal.

After the glass tube containing the sample has been placed into the cooling bath, the helical stirrer is activated. It should be noted that care should be taken to ensure that the stirrer is not raised out of the sample because this can cause air bubbles to form in the sample. As the stirring begins, the temperature of the sample is monitored as it begins to decrease. The temperature of the sample in the tube will decrease at a fairly steady rate. At approximately 10° C. above the expected freezing point of the sample, the cooling rate of the sample is adjusted to maintain it at about 0.1-0.3° C./min. The cooling rate can be maintained by determining the necessary temperature differential between the cooling bath and the sample, then maintaining that difference. As the sample cooling continues at this rate and at near the expected freezing point of the sample, a frozen seed crystal of the sample is added to the contents of the glass tube. When crystals form in the sample, the temperature is recorded as the freezing point only if no super cooling occurs. The temperature of the sample generally stabilizes briefly (for about 10 to about 20 seconds) at the freezing point temperature. If the sample indicates evidence of supercooling, i.e. the temperature rises as crystals form, the freezing point temperature is then taken as the highest temperature after the temperature rise.

The composition and/or aqueous mixture of the present invention are useful in providing biological control in bodies of water, on surfaces, etc. "Surfaces" is used herein in the broadest sense possible and encompasses metal surfaces, human skin, wood surfaces, glass surfaces, fiberglass surfaces, etc. Non-limiting examples of organisms that may be controlled using the liquid biocide of the present invention described above include bacteria, fungi, slime, algae, and mollusks.

A method for disinfecting a surface pursuant to this invention comprises applying a composition and/or aqueous mixture of the present invention to the surface to be disinfected. The composition and/or aqueous mixture may be applied to the surface to be disinfected in various ways. The composition and/or aqueous mixture may be poured directly onto the surface, sprayed onto the surface, or poured, sprayed or soaked onto an applicator, which is then brought into contact with the surface. Applicators include, but are not limited to, cloths, sponges, paper towels, and mops.

A method of treating a body of water pursuant to this invention comprises introducing a concentrated, or partially diluted, composition and/or aqueous mixture of the present invention into the body of water. A variety of methods may be used to introduce the concentrated composition and/or aqueous mixture to the body of water to be treated. The composition and/or aqueous mixture may be added directly to the body of water, either all at once or slowly over time, for example via a pump or feeder. In systems in which the water is circulated through an apparatus, the composition and/or aqueous mixture may be added to this apparatus.

The addition of the composition and/or aqueous mixture of the present invention to the body of water to be treated preferably yields a concentration of composition, biocide and/or aqueous mixture in the body of water in the range of from about 0.1 to about 10 mg per liter of total available halogen, expressed as $Cl_2$. A preferred amount of total available halogen, expressed as $Cl_2$, in the body of water is from about 0.2 to about 4 milligrams per liter. These concentrations of total available halogen, expressed as $Cl_2$, are ordinarily sufficient for treating a body of water and for maintaining microbiological control of a body of water. It should be noted that the amount of composition, biocide, and/or aqueous mixture of the present invention used to treat surfaces and bodies of water will vary depending on the level of biological control sought, the amount of biological organisms present, etc. Thus, it is more preferable that the amount of composition and/or aqueous mixture of the present invention used is a biocidally effective amount.

The above description is directed to several means for carrying out the present invention. Those skilled in the art will recognize that other means, which are equally effective, could be devised for carrying out the spirit of this invention. It should also be noted that preferred embodiments of the present invention contemplate that all ranges discussed herein include ranges from any lower amount to any higher amount. For example, when discussing the freezing point temperature, these ranges can include temperatures in the range of from about 5° C. to about 10° C., in the range of from about −15° C. to about 0° C., in the range of from about −5° C. to about 0° C., in the range of from about 0° C. to about 5° C., etc. The following examples will illustrate the present invention, but are not meant to be limiting in any manner.

EXAMPLES

Example 1

To demonstrate the effectiveness of using at least two metal bases in forming a liquid biocide, a 150 ml beaker equipped with a stirrer was charged with 24.7 g of water and cooled to about 20° C. in an ice bath. Under constant stirring, 20.1 g of an aqueous NaOH solution (50% NaOH) and 16.6 g of KOH pellets (85% KOH) were slowly added to the beaker under constant stirring. 17.6 g of sulfamic acid (99% minimum sulfamic acid) were then added to the beaker contents under constant stirring. After all of the sulfamic acid was added, a clear solution was observed with some white, undissolved solid therein. During the addition of the above reagents, the temperature of the beaker contents was maintained such that they did not exceed 35° C.

21 g of bromine as $Br_2$ were added to the beaker at a rate of about 2 g/minute such that the temperature of the beaker contents never exceeded 38° C. After the bromine addition, a clear orange liquid biocide was observed in the beaker, and the clear orange liquid biocide was removed from the beaker and placed into a 4 oz. high-density polyethylene ("HDPE") bottle. The weight of the liquid biocide was determined to be about 98.3 g. The active bromine content of this liquid biocide was 145,000 ppm (wt./wt.), and the freezing point temperature was about 8° C., as determined by the method discussed above.

Example 2

Freezing Point Comparative 18.8 g of water were added to a 150 ml beaker equipped with a stirrer and cooled to about 20° C. in an ice bath. Under constant stirring, 44.0 g of an aqueous NaOH solution (50% NaOH) were added slowly to the water followed by 16.2 g of sulfamic acid (99% minimum sulfamic acid). During the addition of the NaOH and sulfamic acid, the temperature of the beaker contents was maintained such that they did not exceed 35° C. 21 g of bromine as $Br_2$ were added to the beaker at a rate of about 2 g/minute such that the temperature of the beaker contents never exceeded 35° C. The resulting clear orange liquid biocide was placed into a 4 oz. HDPE bottle, and the weight of the clear orange liquid was determined to be about 99.2 g. The active bromine content of this liquid biocide was 150,000 ppm (wt./wt.), and the freezing point temperature of the liquid biocide was about 19.5° C., as determined by the method discussed above.

Note that the freezing point temperature of the liquid biocide of Example 1, in which KOH was partially substituted for NaOH, was about 11.5° C. lower than the liquid biocide of comparative Example 2, formed by using one metal base, i.e. NaOH.

Example 3

The same procedure outlined in Example 1 above was followed except 32.4 g of water, 5.4 g of KOH pellets, 27.4 g of aqueous NaOH solution, and 13.8 g of sulfamic acid were used. 21.1 g of $Br_2$ were again added to the beaker at a rate of 2 g/minute, and the clear orange liquid biocide thus formed was placed into a 4 oz. high-density polyethylene ("HDPE") bottle. The weight of the clear orange liquid biocide was determined to be about 99.2 g. The active bromine content of this liquid biocide was 146,000 ppm (wt./wt.), and the freezing point temperature of this liquid biocide was about 0.5° C., as determined by the method discussed above.

Example 4

Freezing Point Comparative

The same procedure outlined in Example 2 above was followed except that 28.2 g of water, 36.8 g of aqueous NaOH solution, and 14.0 g of sulfamic acid were used. Also, during the addition of the reagents, the temperature of the beaker contents was maintained at 35° C. 21 g of $Br_2$ were again added to the beaker at a rate of 2 g/minute, and the clear orange liquid biocide thus formed was placed into a 4 oz. high-density polyethylene ("HDPE") bottle. The weight of the clear orange liquid biocide was determined to be about 99.0 g. The active bromine content of this liquid biocide was 143,000 ppm (wt./wt.), and the freezing point temperature of this liquid biocide was about 13.5° C., as determined by the method discussed above.

Note that the freezing point temperature of the liquid biocide of Example 3, in which KOH was partially substituted for NaOH, was about 13.0° C. lower than the liquid biocide of comparative Example 4, and about 19.0° C. lower than the liquid biocide of comparative Example 2, both formed by using one metal base, i.e. NaOH.

Example 5

149.0 g of water were added to a 500 ml round-bottom flask equipped with a stirrer and cooled to about 20° C. in an ice bath. Under constant stirring, 30.6 g of KOH pellets (85% KOH) were added to the water-containing flask followed by 156.0 g of an aqueous NaOH solution (50% NaOH). 78.8 g of sulfamic acid (99% minimum sulfamic acid) were then added to the flask contents under constant stirring. After all of the sulfamic acid was added, a clear solution was observed. During the addition of the reagents the temperature of the flask contents was maintained such that they did not exceed 35° C.

About 37.4 ml of BrCl, generated from the addition of 26.5 g $Cl_2$ and 59.5 g $Br_2$, were added to the flask at a rate of about 1 g/minute such that the temperature of the flask contents never exceeded 35° C. After the BrCl addition, a clear orange liquid biocide was obtained, removed from the flask, and placed into a 500 ml high-density polyethylene ("HDPE") bottle. The weight of the clear orange liquid biocide was determined to be about 496 g.

The active bromine content of the liquid biocide was measured by the method described above and determined to be 169,000 ppm (wt./wt.). The freezing point of this liquid biocide was about 2° C., as determined by the method discussed above.

The liquid biocide having an active bromine content of 169,000 ppm (wt./wt.) was diluted with water to provide a liquid biocide having an active bromine content of about 151,000 ppm (wt./wt.). The freezing point of this liquid biocide was about −12° C., as determined by the method discussed above.

Example 6

Freezing Point Comparative 193.7 g of water were added to a 500 ml round-bottom flask equipped with a stirrer and cooled to about 20° C. in an ice bath. 281.4 g of an aqueous NaOH solution (50% NaOH) were added to the water-containing flask under constant stirring. During the addition of the NaOH, the temperature of the flask contents was maintained such that they did not exceed 35° C. 104.9 g of sulfamic acid (99% minimum sulfamic acid) were then added to the flask contents under constant stirring. After all of the sulfamic acid was added, a clear solution was observed.

About 50 ml of BrCl, generated from the addition of about 38 g $Cl_2$ and 85.7 g $Br_2$, were added to the flask at a rate of about 1 g/minute such that the temperature of the flask contents never exceeded 35° C. After the BrCl addition, a clear orange liquid biocide was observed, and the clear orange liquid biocide was removed from the flask and placed into a 500 ml high-density polyethylene ("HDPE") bottle. The weight of the clear orange liquid biocide was determined to be 703 g.

The active bromine content was measured by the method described above and determined to be 166,000 ppm (wt./wt.). The liquid biocide having an active bromine content of 166,000 ppm (wt./wt.) was diluted with water to provide a liquid biocide having an active bromine content of about 150,000 ppm (wt./wt.). The freezing point of this liquid biocide was about 4° C., as determined by the method discussed above.

Example 7

The same procedure outlined in Example 5 above was followed except that 251 g of water, 83.3 g of KOH pellets, 141.0 g of aqueous NaOH solution (50% NaOH), and 105.0 g of sulfamic acid were used. 50ml of BrCl, generated from 85.7 g $Br_2$ and 38 g $Cl_2$, were again added to the flask at a rate of 1 g/minute, and the clear orange liquid biocide thus formed was placed into a 500 ml HDPE bottle. The weight of the clear orange liquid biocide was determined to be about 694.0 g. The active bromine content was measured by the method described above and determined to be 160,000 ppm (wt./wt.). The liquid biocide was diluted with water to provide a liquid biocide having an active bromine content of about 150,000 ppm (wt./wt.). The freezing point of this liquid biocide was less than about −15° C., as determined by the method discussed above. It should be noted that the freezing point temperature is indicated as less than about −15° C. because the method used to measure the freezing point was stopped at this temperature.

Example 8

In order to determine the effects of the amount of KOH substituted for NaOH in making liquid biocides, the same procedures outlined in Examples 5 and 7 were followed, except the amount of KOH used was varied, as described in Table 1, below. The freeze points of the liquid biocides and active bromine contents are listed in Table 1 also. The mole percents listed in Table 1 are based on the total amount of metal bases used to make the liquid biocide. For example, liquid biocide #1 was formed using 42 mol % KOH, which indicates that 58 mol % NaOH was used.

After the liquid biocides were formed, they were diluted with water to provide for an active bromine content as indicated in Table 1. About 30 g of each liquid biocide were placed in a separate 40 ml glass vial, and the vials were placed in a recirculating cooling bath maintained at a temperature of −5° C. After the samples cooled, frozen seed crystals were added and the samples remained in the bath for a period of about 16 hours. The samples of the liquid biocides were then removed from the cooling bath and analyzed for crystal formation. The results of this experiment are also contained in Table 1 below.

TABLE 1

| Liquid Biocide # | Mole % KOH | Mole % NaOH | Freezing Point Temperature (° C.) | Approximate Active Br Content ppm (wt./wt.) | Approximate % of sample frozen after 16 hrs in −5° C. cooling bath |
|---|---|---|---|---|---|
| 1 | 42 | 58 | <−15 | 150,000 | 0 |
| 2 | 31 | 69 | −11 | 148,000 | 0 |
| 3 | 21 | 79 | −8 | 148,000 | 0 |
| 4 | 10 | 90 | −1 | 149,000 | 5 |
| 5 | 0 | 100 | 4 | 149,000 | 20 |

Example 9

201.8 g of water were added to a 500 ml round-bottom flask equipped with a stirrer and cooled to about 20° C. in an ice bath. Under constant stirring, 31.4 g of $LiOH.H_2O$ powder (98% minimum $LiOH.H_2O$) were added to the water-containing flask followed by 239.1 g of an aqueous NaOH solution (50% NaOH). 107.6 g of sulfamic acid (99% minimum sulfamic acid) were then added to the flask contents under constant stirring. After all of the sulfamic acid was added, a clear solution was observed with some white, undissolved solid therein. During the addition of the LiOH.H$_2$O, sulfamic acid, and NaOH, the temperature of the flask contents was maintained such that they did not exceed 30° C.

About 53 ml of BrCl, generated from the addition of 35.5 g Cl$_2$ and 86.3 g Br$_2$, were added to the flask at a rate of about 1 g/minute such that the temperature of the flask contents never exceeded 35° C. After the BrCl addition, a clear orange liquid biocide was observed, and the clear orange liquid biocide was removed from the flask and placed into a 500 ml HDPE bottle. The weight of the clear orange liquid biocide was determined to be about 699.8 g.

The active bromine content was measured by the method described above and determined to be 168,000 ppm (wt./wt.). An 180 g portion of the 168,000 ppm liquid biocide was diluted with 21.6 g of water to provide for a liquid biocide having an active bromine content of about 150,000 ppm (wt./wt.). The freezing point of this liquid biocide was about −0.5° C., as determined by the method discussed above.

Example 10

Freezing Point Comparative 173.3 g of water were added to a 500 ml round-bottom flask equipped with a stirrer and cooled to 20° C. in an ice bath. Under constant stirring, 299.0 g of an aqueous NaOH solution (50% NaOH) and 107.6 g of sulfamic acid (99% minimum sulfamic acid) were added to the flask contents. After all of the sulfamic acid was added, a clear solution was observed. During the addition of the sulfamic acid, the temperature of the flask contents was maintained such that they did not exceed 30° C.

About 53 ml of BrCl, generated from the addition of 35.4 g Cl$_2$ and 86.4 g Br$_2$, were added to the flask at a rate 1 g/minute such that the temperature of the flask contents never exceeded 35° C. After the BrCl addition, a clear orange liquid biocide was obtained, and the clear orange liquid biocide was removed from the flask and placed into a 500 ml HDPE bottle. The weight of the clear orange liquid biocide was determined to be about 699.5 g.

The active bromine content was measured by the method described above and determined to be 169,000 ppm (wt./wt.). A 18.0 g portion of the 169,000 ppm liquid biocide was diluted with water to provide a liquid biocide having an active bromine content of about 149,000 ppm (wt./wt.). The freezing point of this liquid biocide was about 7.5° C., as determined by the method discussed above.

Example 11

In order to determine the effects of LiOH substitution for NaOH in making liquid biocides, a series of samples was prepared according to the procedures outlined in Example 8 and 9. Still further, the effects of partial substitution of NaOH with both LiOH and KOH were analyzed. The freeze points of the liquid biocides and active bromine contents are listed in Table 2, below. The mole percents listed in Table 2 are based on the total amount of alkali metal bases used to make the liquid biocide. For example, liquid biocide #1 was formed using 20 mol % LiOH, which indicates that 80 mol % NaOH was used for the remainder.

TABLE 2

| Liquid Biocide # | Mole % LiOH | Mole % NaOH | Mole % KOH | Freezing Point Temperature (° C.) | Active Br Content ppm (wt./wt.) |
|---|---|---|---|---|---|
| 1 | 20 | 80 | 0 | −0.5 | 150000 |
| 2 | 5 | 95 | 0 | 6 | 149000 |
| 3 | 10 | 90 | 0 | 3.5 | 149000 |
| 4 | 10 | 80 | 10 | −2.5 | 150000 |

Example 12

In order to determine the effectiveness of re-formulating a commercial biocide to lower the freeze point, a 200 g sample of STABROM® 909 biocide, a liquid biocide commercially available from the Albemarle Corporation, was introduced into a 500 ml beaker equipped with a stir bar and cooled to about 20° C. in an ice bath. A slurry was made by combining 31.2 g of KOH pellets, (85% KOH), 12.9 g of sulfamic acid (99% minimum sulfamic acid), and 31.6 g of water under constant stirring and under conditions such that the slurry temperature never exceeded 35° C. This slurry was added to the STABROM® 909-containing beaker, under constant stirring. 24.4 g Br$_2$, were then added to the beaker, under constant stirring. During the addition of the Br$_2$, the temperature of the beaker contents was maintained such that they did not exceed 30° C.

According to the above-described measurement methods, the STABROM® 909 had an initial active bromine content of 109,000 ppm (wt./wt.) and a freezing point temperature of about −4° C. The reformulated liquid biocide, according to the above-described measurement methods, had an active bromine content of about 129,000 ppm (wt./wt.), and a freezing point of about −9° C. Thus, commercially available liquid biocides can be reformulated to provide for higher bromine concentrations and lower freeze points.

Example 13

Comparative 40.1g of water were added to a 500 ml round-bottom flask equipped with a stirrer and cooled to about 20° C. in an ice bath. 52.6 g of sulfamic acid (99% minimum sulfamic acid) were then added to the flask contents under constant stirring. Under constant stirring, 197 g of KOH solution (50% KOH) were added. During the addition of the reagents, the temperature of the flask contents was maintained such that they did not exceed 26° C. After all of the solution of KOH was added, a white slurry was obtained.

About 26.4 ml of BrCl, generated from the addition of 17.6 g Cl$_2$ and 43.1 g Br$_2$, were added to the flask at a rate of about 1 g/minute such that the temperature of the flask contents never exceeded 35° C. After the BrCl addition, an orange solution with some white solid was obtained. 34.0 g of additional water were added to the flask and a clear orange solution was obtained. The solution was removed from the flask, and placed into a 500 ml high-density polyethylene ("HDPE") bottle. The weight of the clear orange liquid biocide was determined to be about 385 g.

The active bromine content of the liquid biocide was measured by the method described above and determined to be 150,000 ppm (wt./wt.). The freezing point of this liquid biocide was about 9° C. as determined by the method discussed above.

Example 14

26.6 g of water were added to a 500 ml round-bottom flask equipped with a stirrer and cooled to about 20° C. in an ice bath. 88.4 g of sulfamic acid (99% minimum sulfamic acid) were then added to the flask contents under constant stirring. Under constant stirring, 118 g of NaOH solution (50% NaOH) and 166 g of KOH solution (50% KOH) were added. During the addition of the reagents the temperature of the flask contents was maintained such that they did not exceed 35° C. After all of the solution of KOH was added a white slurry was obtained.

About 44.3 ml of BrCl, generated from the addition of 29.6 g $Cl_2$ and 72.4 g $Br_2$, were added to the flask at a rate of about 1 g/minute such that the temperature of the flask contents never exceeded 35° C. After the BrCl addition, an orange solution with some white solid was obtained. The solution was vacuum filtered through a fritted-glass disk to obtain a clear dark orange solution. The solution was removed from the flask, and placed into a 500 ml high-density polyethylene ("HDPE") bottle. The weight of the clear orange liquid biocide was determined to be about 455 g.

The active bromine content of the liquid biocide was measured by the method described above and determined to be 207,000 ppm (wt./wt.). The freezing point of this liquid biocide was about 16° C., as determined by the method discussed above.

Example 15

7.0 g of water were added to a 500 ml round-bottom flask equipped with a stirrer and cooled to about 20° C. in an ice bath. Under constant stirring, 125 g of NaOH solution (50% NaOH) and 176 g of KOH solution (50% KOH) were added. 90.4 g of sulfamic acid (99% minimum sulfamic acid) were then added to the flask contents under constant stirring. During the addition of the reagents the temperature of the flask contents was maintained such that they did not exceed 25° C. After all of the sulfamic acid was added a white slurry was obtained.

About 44.3 ml of BrCl, generated from the addition of 29.6 g $Cl_2$ and 72.4 g $Br_2$, were added to the flask at a rate of about 1 g/minute such that the temperature of the flask contents never exceeded 65° C. After the BrCl addition, an orange solution with some white solid was obtained. The solution was vacuum filtered through a fritted-glass disk to obtain a clear dark orange solution. The solution was removed from the flask, and placed into a 500 ml high-density polyethylene ("HDPE") bottle. The weight of the clear orange liquid biocide was determined to be about 448 g.

The active bromine content of the liquid biocide was measured by the method described above and determined to be 210,000 ppm (wt./wt.). The freezing point of this liquid biocide was about 19° C., as determined by the method discussed above.

Thus, liquid biocides having high active bromine content, i.e. above what has previously been thought possible, as determined by the method described above, can be made, and these biocides remain liquid at room temperature. Heretofore, biocides having active bromine contents this high were never thought possible because it was hypothesized that they would not remain liquid at room temperature.

Example 16

133.3 g of water were added to a 500 ml round-bottom flask equipped with a stirrer and cooled to about 20° C. in an ice bath. 77.4 g of sulfamic acid (99% minimum sulfamic acid) were added followed by 197.9 g of an aqueous NaOH solution (50% NaOH) under constant stirring. A clear solution was obtained. 10.7 g of $Ca(OH)_2$ powder (95% minimum $Ca(OH)_2$) were then added to the reaction mixture producing a white slurry. During the addition of the reagents, the temperature of the flask contents was maintained such that they did not exceed 30° C.

About 35.5 ml of BrCl, generated from the addition of 23.7 g $Cl_2$ and 58.0 g $Br_2$, were added to the flask at a rate of about 1 g/minute such that the temperature of the flask contents never exceeded 30° C. After the BrCl addition, an orange-white slurry was obtained. The slurry was filtered through a 350mL coarse glass fritted funnel to remove solids. The filtrate was then filtered again through a 5 um syringe filter and placed into a 500 ml high-density polyethylene ("HDPE") bottle. The weight of the clear orange liquid biocide was determined to be about 464 g.

The active bromine content of the liquid biocide was measured by the method described above and determined to be 162,000 ppm (wt./wt.).

Example 17

133.6 g of water were added to a 500 ml round-bottom flask equipped with a stirrer and cooled to about 20° C. in an ice bath. 77.4 g of sulfamic acid (99% minimum sulfamic acid) were added followed by 197.8 g of an aqueous NaOH solution (50% NaOH).under constant stirring. A clear solution was obtained. 10.4 g of $Mg(OH)_2$ powder (97% minimum $Mg(OH)_2$) were then added to the reaction mixture producing a white slurry. During the addition of the reagents the temperature of the flask contents was maintained such that they did not exceed 30° C.

About 35.5 ml of BrCl, generated from the addition of 23.7 g $Cl_2$ and 58.0 g $Br_2$, were added to the flask at a rate of about 1 g/minute such that the temperature of the flask contents never exceeded 30° C. After the BrCl addition, an orange-white slurry was obtained. The slurry was filtered through a 350 ml coarse glass fritted funnel to remove solids. The filtrate was then filtered again through a 5 um syringe filter and placed into a 500 ml high-density polyethylene ("HDPE") bottle. The weight of the clear orange liquid biocide was determined to be about 468 g.

The active bromine content of the liquid biocide was measured by the method described above and determined to be 162,000 ppm (wt./wt.).

Example 18

In order to prove the microbiological efficacy of the biocides according to the present invention, two liquid biocides according to the present invention, Formulation A and Formulation B, were used to treat pond water having the properties described in Table 3, below. The two biocides had an active bromine content, as measured by the method described above, of 150,000 ppm (wt./wt.). The liquid biocides used to treat the pond water contained sodium and potassium salts of sulfamic acid.

Formulation A and Formulation B were each individually added to a separate 200 g sample of the pond water until a nominal residual of about 4.0 ppm total residual $Br_2$, as determined by the N,N-diethyl-p-phenylenediamine ("DPD") technique. Actual total residuals, measured after 2 minutes of mixing, varied from 3.6-3.8 ppm. As illustrated in Table 4 below, both formulations provided 1-log reductions in microorganisms (average of data from 1 to 4 hour contact time) under test conditions of room temperature and atmospheric pressures.

TABLE 3

| | |
|---|---|
| pH | 8.41 |
| Conductivity | 0.38 mS/cm |
| TDS | 0.19 g/L |
| Alkalinity | 139 mg/L (as $CaCO_3$) |
| Total Hardness | 10 mg/L (as $CaCO_3$) |

TABLE 4

| | Formulation A | Formulation B |
|---|---|---|
| Initial Bacteria | $2 \times 10^4$ | $2 \times 10^4$ |
| 15 Minute | $6 \times 10^3$ (0.5) | $7 \times 10^3$ (0.4) |
| 1 Hour | $2 \times 10^3$ (1.0) | $3 \times 10^3$ (0.8) |
| 2 Hours | $2 \times 10^3$ (1.0) | $2 \times 10^3$ (1.0) |
| 4 Hours | $1 \times 10^3$ (1.3) | $1 \times 10^3$ (1.3) |
| 24 Hours | $3 \times 10^4$ (NA) | $5 \times 10^4$ (NA) |
| Average (1-4 Hrs) | $1.7 \times 10^3$ (1.1) | $2.0 \times 10^3$ (1.0) |

It should be noted that in Table 4, the total aerobic bacteria counts are in CFU/mL; data in parentheses represent the log reduction relative to the control value of $2 \times 10^4$ (average of 3 determinations).

Example 19

A liquid biocide according to the present invention, Production Sample, was used to treat cooling systems associated with a bromine production facility and an alkyldimethylamine (ADMA) plant. Production Sample had an active bromine content, as measured by the method described above, of 150,000 ppm (wt./wt.), contained sodium and potassium salts of sulfamic acid, and was made in a commercial production facility.

The bromine tower cooling system operated at a ΔT of 20° F. and cycles of concentration of 6, and the ADMA cooling system operated at a ΔT of 8° F. and cycles of concentration of 5. The pH of the recirculating water was in the range of 9.0 to 9.1 units in each cooling system. The amount of Production Sample added to the cooling systems was that amount necessary to maintain the average total residual, ppm as $Cl_2$, as indicated in Table 5.

During the testing, several parameters were monitored on a tri-weekly basis (M-W-F) such as biocide residual (free and total), biocide consumption, pH, conductivity, molybdate, and microbiological performance. Microbiological performance was determined using dipslides (Easicult® Combi). These dipslides provided the ability to monitor for both bacteria and yeast/mold. Other water-quality parameters were determined on a weekly basis such as alkalinity, total hardness, silica, and phosphate. Visual observations were routinely performed of the cooling tower film fill, basin, and recirculating water to detect indications of algae, slime, etc. Table 5 summarizes the field trial results. These trials were conducted for a period of 30 days in each system.

TABLE 5

| | Make-up | Bromine Tower | ADMA Tower |
|---|---|---|---|
| Capacity, gallon | | 60,000 | 35,000 |
| Recirculation Rate, gpm | | 2,500 | 3,200 |
| Make-up | | Well water | |
| Biocide Program | — | Production Sample | Production Sample |
| Tower Parameters | | | |
| Tower ΔT, ° F. | — | 20 | 8 |
| Cycles of Concentration | — | 6.3 | 5.1 |
| pH, units | 8.4 | 9.0 | 9.0 |
| Conductivity, uS/cm | 290 | 1910 | 1930 |
| Alkalinity, ppm | 130 | 780 | 720 |
| Total Hardness, ppm | 4 | 31 | 30 |
| $SiO_2$, ppm | 9.9 | 63.2 | 51.5 |
| $PO_4^{-3}$, ppm | 0.82 | 4.90 | 4.04 |
| Biocide Parameters | | | |
| Consumption, lbs/day | — | 48 | 44 |
| Free residual, ppm as $Cl_2$ | 0 | 0.6 | 0.9 |
| Total residual, ppm as $Cl_2$ | 0 | 1.3 | 1.8 |
| Bacteria, CFU/mL | 0 | mostly $10^0$ | mostly $10^0$ |
| Fungi, CFU/mL | 0 | little/none | little/none |
| Algae | none | none | little/none |
| Corrosion Information | | | |
| $Mo^{+6}$, ppm | — | 1.5 | 2.1 |
| Mild steel corrosion, mpy | — | 0.4 | 1.0 |
| Copper corrosion, mpy | — | 0.6 | <0.1 |

Note:

Data in the table represents averages of multiple data points (except corrosion rate data). Field trials were conducted for 30 days each except for the corrosion data, which represents a time period of 64 days.

What is claimed:

1. An aqueous composition formed from components comprising:
   i) (A) sulfamic acid, and at least two metal bases, which are sodium hydroxide and potassium hydroxide, or sodium hydroxide and lithium hydroxide, or sodium hydroxide, potassium hydroxide, and lithium hydroxide; wherein when the bases are sodium hydroxide and potassium hydroxide, potassium hydroxide is about 10 mol % or more of the total amount of the at least two metal bases, wherein when the bases are sodium hydroxide and lithium hydroxide, lithium hydroxide is about 20 mol % or more of the total amount of the at least two metal bases, and wherein when the bases are sodium hydroxide, potassium hydroxide, and lithium hydroxide, potassium hydroxide is about 10 mol % or more of the total amount of the at least two metal bases and lithium hydroxide is about 10 mol % or more of the total amount of the at least two metal bases; or
   (B) (a) at least one metal salt of sulfamic acid, and (b) at least one metal hydroxide, wherein the metal salt of sulfamic acid (a) has a metal cation, the metal hydroxide (b) has a metal cation that is different from the metal cation of the metal salt of sulfamic acid (a), the metal cations being selected from sodium and potassium, or from sodium and lithium, or from sodium, potassium, and lithium, wherein potassium, when present, is about 10 mol % or more of the total amount of the metal cations (a) and (b), wherein when the metal cations are sodium and lithium, lithium is about 20 mol % or more of the total amount of the metal cations of (a) and (b), and wherein when the metal cations are sodium, potassium, and lithium, lithium is about 10 mol% or more of the total amount of the metal cations of (a) and (b);
   ii) BrCl; and
   iii) water;
   wherein said composition has an active bromine content of between about 148,000 ppm (wt./wt.) and 151,000 ppm (wt./wt.) as BrCl, an atomic ratio of nitrogen to active bromine greater than 1, a pH of at least 7, and a freezing point temperature lower than about 0° C.

2. The composition according to claim 1 wherein said composition has a pH in the range of from about 10 to about 14.

3. The composition according to claim 1 wherein said composition has a pH in the range of from about 12 to about 14.

4. The composition according to claim 1 wherein said composition has a pH in the range of from about 12.5 to about 14.

5. The composition according to claim 3 wherein the atomic ratio of nitrogen to active bromine is in the range of about 1.05 to about 1.4.

6. The composition according to claim 4 wherein the atomic ratio of nitrogen to active bromine is in the range of from about 1.1 to about 1.3.

7. The composition according to any of claims 2-3 wherein the freezing point temperature of the composition is lower than about −5° C.

8. The composition according to claim wherein the freezing point temperature of the composition is in the range of from about −5° C. to about −15° C.

9. A method for disinfecting comprising applying a composition or partially diluted composition according to claim 2 to a surface.

10. The method according to claim 9 wherein said surface is selected from the group consisting of metal surfaces, human skin, wood surfaces, glass surfaces, and fiberglass surfaces, and wherein said composition is applied to said surface by a method selected from the group consisting of pouring directly onto the surface, spraying onto the surface, and pouring, spraying or soaking onto an applicator, which is then brought into contact with the surface.

11. The method according to claim 10 wherein said applicator is selected from the group consisting of cloths, sponges, paper towels, and mops.

12. A method of treating a body of water comprising introducing a concentrated, or partially diluted composition according to claim 2 into a body of water.

13. The method according to claim 12 wherein the addition of the composition to the body of water yields a concentration of the composition in the body of water in the range of from about 0.1 to about 10 mg per liter of total available halogen, expressed as $Cl_2$.

14. The method according to claim 12 wherein the addition of the composition to the body of water yields a concentration of the composition in the body of water in the range of from about 0.2 to about 4 mg per liter of total available halogen, expressed as $Cl_2$.

15. A process comprising:
   A) mixing, in the presence of water,
      i) sulfamic acid,
      ii) at least two metal bases; which are sodium hydroxide and potassium hydroxide, or sodium hydroxide and lithium hydroxide, or sodium hydroxide, potassium hydroxide, and lithium hydroxide;
      wherein when the bases are sodium hydroxide and potassium hydroxide, potassium hydroxide is about 10 mol % or more of the total amount of the at least two metal bases, wherein when the bases are sodium hydroxide and lithium hydroxide, lithium hydroxide is about 20 mol % or more or the total amount of the at least two metal bases, and wherein when the bases are sodium hydroxide, potassium hydroxide, and lithium hydroxide, potassium hydroxide is about 10 mol % or more of the total amount of the at least two metal bases and lithium hydroxide is about 10 mol % or more of the total amount of the at least two metal bases; and
      iii) a $Br^+$ source and a $Cl^+$ source,
   wherein component i) is first mixed with water, and the at least two metal bases ii) are then mixed into the water containing the sulfamic acid, and component iii) is then introduced, thereby forming an aqueous mixture comprising at least soluble and insoluble metal halide salts; and
   B) removing at least a portion of said insoluble metal halide salts from said aqueous mixture,
   wherein i), ii), and iii) are mixed in proportions such that the aqueous mixture comprises predominantly at least two metal salts of a) bromo sulfamate; b) chloro sulfamate; c) halides; d) sulfamates; and e) hydroxides; and said aqueous mixture has an active bromine content of between about 148,000 ppm (wt./wt.) and 151,000 ppm (wt./wt.) as BrCl, an atomic ratio of nitrogen to active bromine greater than 1, a pH of at least 7, and a freezing point temperature lower than about 0° C.

16. The process according to claim 15 wherein said $Br^+$ source is selected from the group consisting of bromine, bromine chloride, hypobromous acid, hypobromite ion, hydrogen tribromide, tribromide ion, and N-brominated compounds.

17. The process according to claim 16 wherein said $Cl^+$ source is selected from the group consisting of elemental chlorine ($Cl_2$), hypochlorite compounds, and N-chlorinated compounds.

18. The process according to claim 17 wherein the atomic ratio of nitrogen to active bromine of said aqueous mixture is in the range of from about 1.1 to about 1.3.

19. The process according to claim 15 wherein iii) is BrCl.

20. The process according to claim 19 wherein the atomic ratio of nitrogen to active bromine of said aqueous mixture is in the range of about 1.05 to about 1.4.

21. The process according to claim 19 wherein the freezing point temperature of said aqueous mixture is lower than about −5° C.

22. The process according to claim 15 wherein the freezing point temperature of said aqueous mixture is in the range of from about −5° C. to about −15° C.

23. A process comprising:
A) mixing, in the presence of water,
   i) at least one metal salt of sulfamic acid;
   ii) at least one metal hydroxide; and
   iii) a $Br^+$ source and a $Cl^+$ source,
   thereby forming an aqueous mixture comprising at least soluble and insoluble metal halide salts; and
B) removing at least a portion of said insoluble metal halide salts from said aqueous mixture,
wherein the metal salt of sulfamic acid i) has a metal cation, the metal hydroxide ii) has a metal cation that is different from the metal cation of the metal salt of sulfamic acid i), the metal cations of i) and ii) being selected from sodium and potassium, or from sodium and lithium, or from sodium, potassium, and lithium, and i), ii), and iii) are mixed in proportions such that the aqueous mixture comprises predominantly at least two metal salts of a) bromo sulfamate; b) chloro sulfamate: c) halides; d) sulfamates; and e) hydroxides;
wherein when the metal cations are sodium and potassium, potassium is at least about 10 mol % or more of the total amount of the metal cations of i) and ii), wherein when the metal cations are sodium and lithium, lithium is about 20 mol % or more of the total amount of the metal cations of i) and ii), and wherein when the metal cations are sodium, potassium, and lithium, lithium is about 10 mol % or more of the total amount of the metal cations of i) and ii); and
wherein said aqueous mixture has an active bromine content of between about 148,000 ppm (wt./wt.) and 151,000 ppm (wt./wt.) as BrCl, an atomic ratio of nitrogen to active bromine greater than 1, a pH of at least 7, and a freezing point temperature lower than about 0° C.

24. The process according to claim 23 wherein said $Br^+$ source is selected from the group consisting of bromine, bromine chloride, hypobromous acid, hypobromite ion, hydrogen tribromide, tribromide ion, and N-brominated compounds.

25. The process according to claim 24 wherein said $Cl^+$ source is selected from the group consisting of elemental chlorine ($Cl_2$), hypochlorite compounds, and N-chlorinated compounds.

26. The process according to any of claim 17 or 25 wherein said hypochlorite source is sodium hypochlorite solution, lithium hypochlorite, or calcium hypochlorite, and wherein said N-chlorinated compounds is trichloroisocyanuric acid or sodium dichloroisocyanurate.

27. The process according to claim 24 wherein iii) is BrCl.

28. The process according to claim 27 wherein said at least one metal hydroxide is sodium hydroxide and potassium hydroxide.

* * * * *